US005733926A

United States Patent [19]

Gorbach

[11] Patent Number: 5,733,926
[45] Date of Patent: Mar. 31, 1998

[54] ISOFLAVONOIDS FOR TREATMENT AND PREVENTION OF ALZHEIMER DEMENTIA AND REDUCED COGNITIVE FUNCTIONS

[76] Inventor: Sherwood L. Gorbach, 31 Perry La., Weston, Mass. 02193

[21] Appl. No.: 766,618

[22] Filed: Dec. 13, 1996

[51] Int. Cl.$^6$ ..................................................... A61K 31/35
[52] U.S. Cl. .................................................. 514/456; 514/457
[58] Field of Search ........................................... 514/456, 457

[56] References Cited

U.S. PATENT DOCUMENTS 5,276,054  1/1994  Diez et al. ............................... 514/455
5,589,182  12/1996  Tashiro et al. ........................... 424/423

*Primary Examiner*—Theodore J. Criares
*Attorney, Agent, or Firm*—Clark & Elbing LLP

[57] ABSTRACT

A method of treating or preventing, in a human patient, dementia of Alzheimer type, or age-related loss of cognitive function, said method comprising administering to said patient an isolated isoflavonoid selected from the group consisting of genistein, daidzein, biochanin A, formononetin, O-desmethylangolensin, glycitin, and equol, in an amount sufficient to produce a transient isoflavonoid concentration in the bloodstream of said patient of at least 100 nanomoles/L.

18 Claims, No Drawings

ISOFLAVONOIDS FOR TREATMENT AND PREVENTION OF ALZHEIMER DEMENTIA AND REDUCED COGNITIVE FUNCTIONS

BACKGROUND OF THE INVENTION

The present invention relates to therapies for the prevention and treatment of dementia and reduced cognitive functions associated with advancing age.

It has long been recognized that dementia and diminished cognitive performance develop in persons over 65 years of age and these problems increase in frequency as the aging process advances. While these changes in cognitive behaviors are seen with the same frequency everywhere in the world, the types of dementing conditions differ in geographical areas. Thus, dementia of Alzheimer disease is more common than dementia of vascular disease in North America and Europe, while the dominant pattern in Japan is vascular dementia which is nearly twice as common as Alzheimer dementia. Another factor that influences cognitive functions in older women is the use of estrogen replacement therapy (ERT). The risk of developing Alzheimer disease and related dementia is less in women who use ERT after the production of their own estrogen hormones declines at the time of menopause. Cognitive function is improved in women who are given ERT for treatment of their dementia. Other drug treatments have been developed for Alzheimer dementia, but they are not fully effective and are associated with side effects. Safer and effective therapies for treating and preventing dementia and reduced cognitive function continue to be sought.

SUMMARY OF THE INVENTION

The invention features the use of isolated isoflavonoids, which are constituents of soy beans and other plants such as clover, to treat and prevent dementia of the Alzheimer type, as well as other reduced cognitive functions associated with advancing age. Without being bound by any theory, it is believed that isoflavonoids have significant estrogenic activity, acting in the brain by enhancing neurotransmission and restoring synaptic density. It is believed that isoflavonoids are active in the brain at the same site as estrogen, exerting an estrogenic response. These compounds are safe and cause no significant side-effects. Isoflavonoids which may be administered according to the invention include genistein, daidzein, biochanin A, formononetin, O-desmethylangolensin, glycitin, and equol; these may be administered alone or in combination. The isolated isoflavonoid may be administered in any suitable form, e.g., in the form a plant extract rich in isoflavonoids or in the form of a purified or synthesized isoflavonoid. By "isolated" is meant the isoflavonoid is in a form which is more concentrated than the form in which it occurs naturally in plants. Treatment according to the invention is carried out using a therapeutic dietary product or a medicament form of one or more isolated isoflavonoid. The dietary product preferably includes a soy or plant extract enriched in isoflavonoids, provided in a palatable food carrier, e.g., a confectionary bar, biscuit, cereal or beverage. The medicament form preferably takes the form of a pill, tablet, capsule or powder, or a liquid or syrup formulation.

Other features and advantages of the invention will be apparent from the Detailed Description thereof, and from the claims.

DETAILED DESCRIPTION

Isoflavonoids are naturally occurring substances, found primarily in soy beans. These compounds can also be found in high concentrations in red clover and in lower amounts in many other types of plants. An isoflavonoid-containing fraction useful in the invention can be extracted from a soy or plant product. It is preferred that the isoflavonoids be extracted and concentrated from soy bean or soy powder, but other plants such as clover can be used. Isoflavonoids are also available commercially in substantially pure form. The concentrated isoflavonoid is preferably included in a food carrier to form a dietary product. Any type of palatable carrier may be used, but as the isoflavonoid concentrate has a strong flavor, it is preferred that the carrier include suitable flavorings to impart a different, more palatable flavor. The dietary product may be any type of food product, e.g., a confectionary bar, biscuit, cereal or beverage.

It is preferred that the dietary product contain at least 20 mg/serving total isoflavonoids. The isoflavonoid concentrate included in the dietary product preferably includes a blend of isoflavonoids with genistein, daidzein, biochanin A, formononetin, O-desmethylangolensin, glycitin, and equol; these may be administered alone or in combination. Preferably, a dietary product containing the preferred dosage of isoflavonoids is consumed at least once per day, more preferably 2 times per day for more severe symptoms.

The isoflavonoid also can be administered, preferably in similar dosages, in medicament form, e.g., mixed with a pharmaceutically acceptable carrier to form a pill, tablet, capsule or powder, or a liquid or syrup formulation.

When isoflavonoids are fed to healthy American adults, the absorption into the bloodstream is 10 to 20% of the amount consumed. This produces blood levels of isoflavonoids 200 to 2000 times higher than the levels of the most active natural estrogen in women, estradiol. It is known that the estrogenic activity of isoflavonoids is about 1000 to 10,000 lower than that of estrogen contained in estrogen replacement therapy. These determinations indicate that consumption of isoflavonoids in dosages of 20 to 50 mg per day provides blood levels with estrogenic activity in the range of that found with estrogen replacement therapy.

Other embodiments are within the claims.

I claim:

1. A method of treating or preventing, in a human patient in need thereof, dementia of Alzheimer type, or age-related loss of cognitive function, said method comprising administering to said patient an isolated isoflavonoid selected from the group consisting of genistein, daidzein, biochanin A, formononetin, O-desmethylangolensin, glycitin, and equol, in an amount sufficient to produce a transient isoflavonoid concentration in the bloodstream of said patient of at least 100 nanomoles/L.

2. The method of claim 1 wherein said isoflavonoid is administered in a dosage of at least 20 mg.

3. The method of claim 2 wherein said isoflavonoid is administered at least once per day.

4. The method of claim 1 wherein there is administered to said patient at least one of genistein, daidzein, biochanin A, formononetin, O-desmethylangolensin, glycitin, or equol.

5. The method of claim 1 wherein said isoflavonoid is administered in the form of a non-naturally occurring dietary product.

6. The method of claim 5 wherein said isoflavonoid contains at least 20 mg/serving of said isoflavonoid.

7. The method of claim 5 wherein said dietary product is a confectionary bar.

8. The method of claim 5 wherein said dietary product is a cereal.

9. The method of claim 5 wherein said dietary product is a biscuit.

10. The method of claim 5 wherein said dietary product is a beverage.

11. The method of claim 1 wherein said isoflavonoid is administered in the form of a medicament.

12. The method of claim 11 wherein said medicament contains at least 20 mg/serving of said isoflavonoid.

13. The method of claim 11 wherein said medicament is in the form of a pill.

14. The method of claim 11 wherein said medicament is in the form of a tablet.

15. The method of claim 11 wherein said medicament is in the form of a capsule.

16. The method of claim 11 wherein said medicament is in the form of a powder.

17. The method of claim 11 wherein said medicament is in the form of a liquid or syrup.

18. The method of claim 11 wherein said medicament is consumed by said patient at least once per day.

* * * * *